United States Patent [19]
Wellinghoff

[11] Patent Number: 5,372,796
[45] Date of Patent: Dec. 13, 1994

[54] METAL OXIDE-POLYMER COMPOSITES

[75] Inventor: Stephen T. Wellinghoff, San Antonio, Tex.

[73] Assignee: Southwest Research Institute, San Antonio, Tex.

[21] Appl. No.: 47,750

[22] Filed: Apr. 13, 1993

[51] Int. Cl.$^5$ ............................................. C03C 3/00
[52] U.S. Cl. ................................. 423/65; 423/338; 501/12; 501/134; 501/905; 252/315.2
[58] Field of Search .................. 501/12, 134, 905; 252/315.01, 315.1, 315.2; 423/338, 62, 65, 66

[56] References Cited

U.S. PATENT DOCUMENTS 4,849,140  7/1989  Wellinghoff et al. ............... 264/9
5,160,455  11/1992  Clark et al. ....................... 252/315.7

*Primary Examiner*—Helene Klemanski
*Assistant Examiner*—Chris Gallo
*Attorney, Agent, or Firm*—John L. Sigalos

[57] ABSTRACT

A method of making metal oxide clusters in a single stage by reacting a metal oxide with a substoichiometric amount of an acid in the presence of an oxide particle growth terminator and solubilizer. A method of making a ceramer is also disclosed in which the metal oxide clusters are reacted with a functionalized polymer. The resultant metal oxide clusters and ceramers are also disclosed.

11 Claims, No Drawings

METAL OXIDE-POLYMER COMPOSITES

This invention was made under contract No. NAG-9-229 with the National Aeronautics and Space Administration Association (NASA).

BACKGROUND OF THE INVENTION

The present invention relates to novel metal oxide clusters, ceramers made therefrom, and to the methods of making the same.

Polymer-ceramic composites or ceramers have the potential to combine the properties of polymers and ceramics, particularly oxides, in useful ways. Of special use are the so called nanocomposites which consist of alloys of polymers with ceramic particles of diameter much smaller than the wavelength of visible light. High refractive index, scratch and corrosion resistant optical coatings and radiation resistant coatings are such applications.

These inorganic/organic hybrid materials have been prepared by:

1) reacting an oligomer functionalized by a trialkoxysilane with a metal alkoxide and a water generating source in a single step to make a "ceramer";
2) prereacting an organofunctionalized (epoxy, alkenes, etc) trialkoxysilane with a metal alkoxide and a water generating source to generate an "ormocer" in the first step and then fusing these organocoated inorganic oxide clusters into a solid body by polymerization of the organic groups in the second step;
3) swelling a metal alkoxide into a preformed elastomer and subsequently hydrolyzing the alkoxide to oxide; and
4) preparation of a highly porous xerogel by hydrolysis of dilute metal alkoxides and subsequent infiltration and polymerization of monomer in the pores.

Methods 1, 2, 3 have so far been used only for thin film coatings since a large surface must be available, permitting small molecule condensation products to evaporate during alkoxide hydrolysis and self-condensation into the oxide. Method 2 is an extension of Method 1 since an oxide cluster is also surface functionalized by an organic functional group. However, in Method 2, the small molecule condensation products are completely removed from the cluster in a separate step prior to fabrication.

Recently the detailed structure of soluble alkoxide coated titanium oxide and trialkyl siloxane coated, hydroxy aluminum hydroxide ormocers have been elucidated. All useful ormocer materials are soluble in organic solvents and can be cast into films.

In an especially useful application of ormocer materials, oxide clusters coated with photopolymerizable groups have been fabricated into high refractive index, optical waveguides by photolithography.

In all applications so far the ormocers have been first solvated and solvent cast. In principal, compression molding of the organic coated clusters should be possible, thus opening the way for the manufacture of thick plaques which can now be made only by Method 4.

X-ray absorbing windows are presently manufactured from melt casting silica based glass of high PbO content or methylmethacrylate-methacrylic acid ionomers containing $Pb^{+2}$ counterion. Although these absorbing windows are effective, the presence of lead makes them unsuitable for contained environments such as are present in space or undersea applications.

BRIEF DESCRIPTION OF THE INVENTION

The subject of the present invention solves this problem by permitting compression molding of thick plaques of environmentally safe, one phase alloys of metal oxide clusters with high X-ray absorption and a functionalized polymer.

Briefly, metal oxide clusters are formed by reacting a metal alkoxide, $M(OR)_n$, with a substoichiometric amount of a non-aqueous acid and an oxide particle growth terminator and solubilizer.

The novel clusters are reacted with a functionalized polymer which grafts onto the metal oxide clusters to form novel ceramers.

DETAILED DESCRIPTION

While the present invention is carried out using any metal capable of forming amphoteric metal oxides, such as tantalum, niobium, indium, tin, and the like it will be described in connection with tantalum. Also, as to the alkoxy group utilized, it can be a $C_1$-$C_3$ alkoxy group, it is preferred to use an ethoxy group so that the preferred alkoxide used in forming the clusters and resultant ceramers is tantalum ethoxide.

As to the acid used in the reaction it is preferred to use formic acid, although any acid can be utilized whose ester resulting from the reaction with the metal alkoxide has a low vapor pressure; a vapor pressure such that it will evaporate below about 200° C.

The growth terminator and solubilizer used is preferably $ClSi(CH_3)_3$, although again any terminator also having a low vapor pressure as noted above with respect to the acid, can be utilized. Thus, tri-alkyl silane esters can be utilized, as can the chlorosilanes in which other alkyl groups, $C_2$-$C_7$, are substituted for the methyl group. In like manner suitable terminators include chloroalkyl compounds in which the Si is substituted by any metal or non-metal which can form monofunctional compounds, such as tin, indium, aluminum, sulfur, and the like.

The functionalized polymer can be any thermoplastic or thermosetting polymer that has been functionalized so as to be capable of reacting with the metal oxide cluster. The functional group is preferably a hydroxyl group, although, epoxy, acidic, amino groups and the like can also be utilized. It is preferred to use thermoplastic hydroxyl functionalized phenoxy polymers. Also, as used herein the term "polymer" includes oligomers.

The synthesis of transparent composites of tantalum oxide and a polymer requires that the oxide clusters be on the order of 1/10 the scale of visible light, that they be soluble in a common solvent with the matrix polymer, and interact with the polymer matrix exothermically to maintain a compatible single phase blend. Melt processing also requires that the tantalum oxide phase be the discreet phase within a continuous phase of linear polymer. Of course films can be cast of any composition provided that the components are compatible.

It is clear that solid state ductility and impact strength will also be promoted by a high matrix polymer content. However, high tantalum contents are necessary for high X-ray absorption. Chemical resistance to aggressive hydrolytic solvents such as hydrazine and hydrazine hydrate is possible only if both the tantalum oxide and polymer components and the interfacial bond between them is resistant. The requirements for the manufacture of a successful material for space applications are clearly severe.

The structure of tantalum oxide oligomers has been explored several years ago and soluble tantalum oxide ethoxide oligomers were prepared by hydrolyzing tantalum ethoxide in alcohols and benzene. In these cases the tantalum maintains a (+5) oxidation state and hexaco-ordination with oxide, and ethoxide-either bonded by a primary or co-ordination bond with solvent.

The oligomers became insoluble at degrees of hydrolysis, $1.56 < h < 1.69$ depending on solution concentration at which point the models predicted a rapidly increasing molecular weight with added hydrolysis. The stoichiometry predicted by the equation, $$Ta(OEt)_5 + 2.5H_2O \rightarrow \tfrac{1}{2} Ta_2O_5 + 5EtOH, \qquad 1)$$

is obtained only by a model at the hexamer stage.

There is considerable evidence that the Ta—OR and the Ta—O(H)R co-ordinative bonds are quite labile in the presence of other alkoxide species. Reaction with organic esters is also possible by transesterification and reaction with β diketones and ketone esters. A typical transesterfication reaction is:

$$Ta(OEt)_5 + 5Me_3SiC(O)OMe \rightarrow Ta(OSiMe_3)_5 + 5EtC(O)OMe \qquad 2)$$

Most linear, amorphous polymers that contain aryl or arylalkyl ether linkages exhibit high impact strength and ductility between a high $T_g$ and a subambient, backbone β relaxation that originates in the aryl or alkyl oxygen linkage. The linear hydroxy polyether made by reacting bisphenol A and epichlorohydrin in base (phenoxy polymer) behaves in this fashion with a $T_g$ of 100° C. and considerable room temperature ductility. Unlike polycarbonate of bispenol A, the phenoxy polymers are hydrolytically stable.

The secondary hydroxyl has the potential to react by the formation of esters or ethers, and thus, with the Ta—OR bond.

Tantalum ethoxide is reacted with formic acid according to the stoichiometry for the reaction:

$$Ta(OEt)_5 + 2.5\, HC(O)OH \rightarrow \tfrac{1}{2} Ta_2O_5 + 2.5\, HC(O)OEt + 2.5\, EtOH \qquad 3)$$

NMR indicates that hydrolysis of the tantalum ethoxide is almost instantaneous. As the reaction proceeds the single hydroxylic resonance moves upfield until visual gelation at 20 min. The gel that forms at this time is quite transparent and there is no clear phase separation. However, the hydroxylic NMR splits into two resonances at this time-a sure sign of phase separation into a mobile and a viscous phase. At 20 min the narrow resonance at 7.3 ppm collapses and a broader peak at 7.17 ppm suddenly appears in addition to a small remaining, narrow peak in the mobile phase at 7.27 ppm. Increased width of the resonance occurs as the dipolar broadening increases in a new phase of higher viscosity until the viscous phase peak disappears into the backround between 30–60 minutes. This suggests that some unreacted hydroxylic species (Ta—OH, EtOH) are incorporated into a viscous, almost solid phase.

Both the tantalum formate and tantalum ethoxide-methylene protons decrease in intensity and broaden into the backround, consistent first with a polymerization and then formation of a tantalum rich phase at 20 minutes.

At 8.2 ppm the ethyl formate formyl proton increases at the expense of the formic acid formyl proton. The line shapes are always narrow, consistent with both of these species being in the mobile phase. The observation that changes continue in this region past 20 minutes is a sign that the reaction hydrolysis can still occur in the viscous phase.

In order to measure the extent of reaction the integrated area of the ethyl formate methylene peaks at 4.3 ppm with the ethanol methylene peaks at 3.75 ppm was ratioed. The reaction goes to completion in about 80 minutes, at which time the ethyl formate to ethanol ratio approximates the expected 1:1 ratio.

Once the reaction has gone to completion, the gel is insoluble in all organic solvents after the volatile reaction products have been removed (alcohols, ethers). Addition of 50% of the required formic acid from equation (3) generated solutions which never gelled at RT (heating to 40° C. initiated gelation) while 75% of the required formic acid yielded solutions that gelled after 1 hr at RT.

As mentioned above insoluble species were generated when the reaction of the ethoxide was carried out with formic acid alone. Therefore, chloro trimethyl silane was included in the reaction with the expectation that a reaction similar to reaction (2) would cap the growing tantalum oxide phase at a soluble stage.

$$(Me)_3SiCl + HCOOH \rightarrow (Me)_3SiO(O)CH + HCl \qquad 4)$$

$$(Me)_3SiO(O)CH + -TaOEt \rightarrow$$
$$-Ta-OSi(Me)_3 + HC(O)OEt$$

$$(Me)_3SiO(O)CH + -TaOH \rightarrow$$
$$-Ta-OSi(Me)_3 + HCOOH$$

Because of a lability of the Ta—O—Si bond, replacement with other alcohols was expected to be easy, with the driving force being the condensation of the displaced trimethyl silanol to form the volatile hexamethyldisiloxane.

$$2(Me)_3SiOH \rightarrow (Me)_3Si-O-Si(Me)_3 + H_2O \qquad 5)$$

When the stoichiometries dictated by reaction 3 were employed insoluble products were obtained However, when only 75% of the formic acid required for reaction 3 was added, soluble gel powders were obtained from the initially clear monolithic gel (Ta—O—Si).

The powder with tantalum oxide weight percentages less than 60% (to 60Ta-40 phenoxy) can be compression molded at 150° C. into transparent plaques.

Although UV-visible spectroscopy reveals no change of the optical transparency of the 60 Ta-40 phenoxy upon exposure to $N_2H_2$—$H_2O$ for two hours at room temperature there are some minor changes observed in the IR spectrum of exposed thin films.

The 60Ta-40 phenoxy films can be cast onto polycarbonate of bisphenol A (PC) and the plaque molded to produce a sandwich arrangement which has the potential for high X-ray absorption windows with chemical resistance and good mechanical and optical properties.

The FTIR spectra of the Ta—O—Si powder revealed Ta—O stretching at 1000-600 cm$^{-1}$, hydroxide peaks at 3500 and 1600 cm$^{-1}$. Superimposed are the narrow peaks at 1250, 840, 800 and 750 cm$^{-1}$ due to the Si(Me)$_3$ vibrations. Heating up to 200° C. does not remove the silane vibrations, indicating bonding through Ta—O—Si. However, heating does remove OH vibrational intensity and ultimately leads to insolubility of the powder in methoxyethanol. Condensation of excess surface Ta—OH to extended network Ta—O—Ta probably accounts for this. Attempts to postreact the hydroxyl groups of Ta—O—Si with refluxing $(Me)_3$SiCl for 12 hrs was unsuccessful, probably because most of the hydroxyls were internal to the tantalum oxide cluster.

The Ta—O—Si powder could be readily dissolved in refluxing 2-methoxyethanol. FTIR of cast films showed that the Ta—OSi$(Me)_3$ groups had been replaced by Ta—$OCH_2CH_2OMe$ (triplet at 1100 $cm^{-1}$-ether oxygen stretch). After 12 hrs at 200° C. in air the organic component was completely removed; however almost complete elimination of the hydroxy group was obtained after only 15 min at 200° C. Amorphous tantalum oxide stretching vibrations represented the only remaining peaks. Apparently the methoxyethoxide group is less strongly bound to the Ta center than the siloxyl group.

Similar behavior was noted for the cast ethanol solutions of Ta—O—Si (doublet at 1100 $cm^{-1}$ - ether stretch). In all cases clear films were formed that tended to crack upon drying at film thicknesses over 10 microns.

In an experiment to determine the lability of the Ta—O—$CH_2CH_2OMe$ bond, a solution of the methoxyethoxide derivative was dissolved in $CD_3OD$. An NMR of the solution revealed the presence of methoxyethanol and a very small amount of hexamethyldisiloxane. The lack of any other tantalum phase resonances was evidence for $CD_3$—O—Ta bound to the surface of a oxide cluster with no internal rotational flexibility. The NMR was calibrated so that the absolute amount of methoxyethanol released by dissolution in the deuterated methanol could be calculated.

In order to calculate the composition of the methoxyethoxide complex we must assume a structural model and assume all the methoxyethoxide groups have been replaced by $CD_3O$—. Since the evidence seems strongest for the formula in FIG. 1a we chose this model and calculated the average composition to correspond to an quatermer, n=4, $Ta_{10}O_{12}(OCH_2CH_2OCH_3)_{26}$ (Ta—O—MOEO).

The susceptibility of Ta—O—MOEO to substitution by methyl alcohol provided a rational for codissolution with phenoxy polymer with the expectation that, upon casting, the secondary hydroxyl of the phenoxy polymer would displace the methoxyethanol and form a single phase blend. The only concern was that the degree of substitution, and consequently crosslinking, would be too great at an early stage, thus preventing useful processing such as compression molding which requires a thermoplastic like continuous phase. The reaction with the functionalized polymer is carried out in any alcohol that is a solvent for both the oxide and the polymer, such a 2-methoxyethanol and the like.

A 60Ta-40phenoxy film cast at 100° C. is transparent between 400-2700nm (A 2800 nm absorbance is an OH vibrational absorbance). The absorbance starting at wavelengths shorter than 400 nm originates in the Ta—O—Ta bond. It is present in neat $Ta_2O_5$ gels derived from the formic acid process (50 Ta(OEt)$_5$:50 HCOOH) and starts to intensify and shift into the visible with heating and probably results from impurity states having a charge transfer character (Ta(+5)<->Ta(+4)). A light yellow color is apparent in 2 mm thick plaques (60Ta-40phenoxy) compression molded at 150° C. In gels derived with excess formic acid these centers are not quenched to a transparent state by atmospheric oxygen until 550° C. ($T_{crystallization}$=720° C.).

The vibrational spectra of neat polymer films of phenoxy polymer and 60Ta-40phenoxy were obtained. Digital subtraction of the phenoxy component from the 60Ta-40phenoxy film was employed to isolate the tantalum oxide component.

In the isolated tantalum oxide spectra the free phenoxyhydroxyl vibration at 3600 $cm^{-1}$ decreases along with the phenoxyhydroxyl bending vibration at 1240 $cm^{-1}$. The broad hydrogen bonded hydroxyl vibration at 3200 $cm^{-1}$ is quite apparent in both spectra with a slight decrease being noted as the film is further "cured" at 80° C. A new band appears at 1100 $cm^{-1}$ which can be assigned to Ta—O—CH—(phenoxy polymer) C—O ether stretch vibration. All of these spectral changes are consistent with conversion of phenoxy-OH to hydrogen bonded phenoxy-OH and ether linkages with tantalum.

The broad Ta—O—Ta vibrations at 800 $cm^{-1}$ and 600 $cm^{-1}$ are reversed from their normal intensity ratios. In neat amorphous tantalum oxide the vibrations of Ta—O for Ta in a pentagonal bipyrimidal site (600 $cm^{-1}$) is normally more intense than those vibrations originating from Ta—O for Ta in an octahedral site. Clearly the bonding with the phenoxy polymer induces a considerable structural modification in the tantalum oxide cluster.

The trialkyl siloxane coated tantalum oxide nanoclusters have the general formula $Ta_xO_y(OSiR_3)_z$ in which $1<y/x<2.5$ and $1<z/y<2$ and the alkoxide coated nanoclusters have the general formula $Ta_xO_y(OR)_z$ in which R is a lower alkyl, methoxyalkyl, or ethoxyalkyl group and $1<y/x<2.5$ and $1<z/y<2$.

The invention will be described in connection with the following examples which are set forth for purposes of illustration only.

EXAMPLE 1

Preparation of Tantalum Oxide Clusters-Phenoxy Polymer Blends 4 ml of Ta(OEt)$_5$ (Aldrich) were added by dry transfer techniques from a storage schlenk under nitrogen to the reaction schlenk. Next 1 ml of dry $(Me)_3$SiCl (Aldrich) was mixed with the ethoxide with magnetic stirring followed by 1.25 ml of 96% formic acid (Aldrich). Stirring was continued under nitrogen for 1.5 hrs at RT, at which time a clear gel formed. The gel was permitted to react at RT for an additional 6-12 hrs before dynamic vacuum was applied to remove the reaction products.

The gel rapidly fractured as soon as the vacuum was applied and, after an additional 8-12 hrs under vacuum and stirring with a magnetic stir bar, a fine powder was obtained of composition $Ta_xO_y(OSiMe_3)_z$ (Ta—O—Si). This powder was stable for months under nitrogen and was soluble 4-5% by weight in 2-methoxyethanol, ethanol, and methanol and insoluble in non-hydrolytic polar solvents such as dimethylformamide, dimethylsulfoxide and acetonitrile.

The Ta—O—Si powder was dissolved in boiling 2-methoxyethanol to form a clear solution of 4% weight fraction. This solution was mixed at different volume ratios with 10 wt % solution of 67,000 MW phenoxy polymer (Polysciences) in 2-methoxyethanol and cast into thin films on glass, AgCl or KBr at 100° C. or vacuum rotoevaporated at 80° C. to form a clear film of the blend.

Films with more than 80 wt % of added Ta—O—Si were brittle and could be powdered at room temperature. However, films with lower added Ta—O—Si contents were ductile and were powdered at liquid nitrogen temperatures.

Powders with 60% added Ta—O—Si or less could be vacuum compression molded into multimillimeter thick plaques. In a typical procedure 0.6 g of powder is placed within a 1.2 cm diameter compression die with removeable base disk and sealed with a piston. This whole assembly is placed within a vacuum die of 5.6 cm diameter with a heating jacket controlled by a Chromalox controller (Carver). The die is sealed with the top piston evacuated and heated to 100° C. to remove any volatiles.

After pressurizing to approximately 10,000 psi (Carver press) the die is heated to 150° C. and molded for approximately 20 minutes. The dies are then disassembled and the inner die assembly is quenched into water. The polymer-oxide plaque is then removed.

EXAMPLE 2

Chemical Resistance of the 60Ta-40phenoxy Films

Some ductile polymers such as polycarbonate of bisphenol A are quite susceptible to cleavage by strong bases which can lead to degradation of their normally good optical properties. Phenoxy polymer is known to be chemically resistant to strong acids and bases but to be soluble in polar organic solvents. Experience with cured Epon 828 polymers and composites suggests that free hydroxide does make the polymers somewhat susceptible to swelling by water especially at high temperatures.

In the way of testing the hydrolytic stability of the 60Ta-40phenoxy films were immersed in hydrazine hydrate for 2 hours at room temperature-needless to say a very severe test. Under the same conditions polycarbonate undergoes severe hydrolytic attack with substantial permanent fogging of the surface. There was no change in the UV-vis spectrum of the exposed film. However, there were some small changes noticed at 3600 cm$^{-1}$ which is the vibration due to unbonded —OH. This generation of free hydroxyl could have originated from debonding of the phenoxy-OH from the tantalum cluster surface. Some recovery of this OH bonding was noticed after reheating the film for 48 hrs at 80° C.

EXAMPLE 3

X-ray Absorption Characteristics of Plaques

The clear advantage of heavier elements is their ability to absorb photons in the range below 1 MeV through photoelectric processes and Compton scattering and above 10 MeV by electron-positron production. The principal source of energetic photons is the Bremsstrahlung radiation produced by deacceleration of multi-MeV electrons by the nucleus. Little difference between carbon and lead in absorption coefficient on the gram per cubic centimeter is seen between 1 and 10 MeV since almost all the contribution to absorption comes from Compton scattering. In this range a heavy element increases the absorbance, -Log(I/I$_o$), in almost direct proportion to the density increase it imparts to the material. For instance 1 cm of lead has an absorbance of 0.14 for 10 MeV gamma rays while 1 cm of diamond has an absorbance of 0.03.

However, orders of magnitude differences are seen below 0.2 MeV in the region of characteristic X-ray absorption of the elements by photoelectric excitation. Large wavelength dependent absorption coefficient changes occur for a given element at energies ("absorption edges") where the photon has enough energy to ionize an inner shell electron. For the heaviest elements the K shell ionization energy can reach 0.1 MeV. The element then relaxes by emitting characteristic X-rays which are also absorbed most efficiently by the heavier elements. The net effect is that the initial energy of the gamma photon is dissipated in the plaque. The radiation dosage in rad units is the result of all unabsorbed photons of significant energy that emerge from the back end of the plaque. The most advantageous absorber is one that contains the highest percentage of heavy element. A thickness of several times the kinematic absorption length for the first photon permits multiple readsorption of multiple-inelastically, scattered photons.

In order compare how effectively the Ta plaque with 60% Ta$_2$O$_5$ compares with a phenoxy polymer film of the same thickness the absorbance of a 1 cm thick plaque for 0.1 MeV and 1.0 MeV photons was calculated. The mass absorption coefficients of the various elements were used to calculate the absorbance of the composite material for different weight percentages of Ta$_2$O$_5$. The expected composite density is calculated by assuming that:

$$\rho_{comp} = V_a\rho_a + V_b\rho_b, \qquad 6)$$

where a and b are tantalum oxide and phenoxy polymer and $\rho_i$, and $V_i$, are the density and volume fraction of the components.

The expected absorbance for a 1 cm plaque of 60Ta is about 0.5 at 0.1 MeV and about 0.013 at 10 MeV. The absorbance of the positron annihilation gamma at 0.5 MeV would be about 0.04 for 60Ta as opposed to the 0.13 expected for pure tantalum oxide. This again verifies that any practical composite face shield would be useful only for radiation below 0.2 MeV.

EXAMPLE 4

The procedure of Example 1 is carried out except that an equivalent amount of tin and indium are substituted for the tantalum in the alkoxide.

Equally good composites are formed with the phenoxy polymer.

It will be understood that specific proportions of reactants, reaction times, and reaction conditions for optimum results may vary somewhat for different metal alkoxides, acids, polymers, and other reactants used. The optimum conditions can be determined by routine experimentation utilizing the specifics as to tantalum, ethoxide, formic acid, phenoxy polymer and trimethylchlorosilane set forth herein.

In addition to use in high refractive index, X-ray absorbency optical elements for space and military applications, the products of this invention have other applications. Thus, tantalum species can be used as optical wave guides, and corresponding tin and indium species be used as corrosion resistant coatings, transparent electrically conducting plaques, and the like.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A method of making a metal oxide cluster in a single stage comprising reacting a metal alkoxide with a substoichiometric amount of an acid in the presence of an oxide particle growth terminator and solubilizer and in the absence of water at a temperature and for a time sufficient to form a metal oxide of cluster gel.

2. The method of claim 1 including the step of forming said gel into a fine powder in vacuum until substantially all volatiles are removed.

3. The method of claim 1 wherein the metal alkoxide has the general formula $M(OR)_n$ wherein M is a metal capable of forming amphoteric oxides, R is a $C_1$-$C_3$ alkoxy group, and n is an integer.

4. The method of claim 3 wherein said acid is selected from acids whose esters resulting from the reaction with said metal alkoxide have a vapor pressure such that they will evaporate at a temperature below about 200° C.

5. The method of claim 4 wherein said oxide particle growth terminator and solubilizer has a vapor pressure such that it will evaporate below about 200° C.

6. The method of any one of claims 1 to 5 wherein the reaction is carried out at room temperature, said metal alkoxide is a tantalum alkoxide, said acid is formic acid, and said oxide particle terminator and solubilizer is a trialkyl chlorosilane.

7. The metal oxide cluster produced by the method of claim 1 in the form of a gel or powder.

8. The product of claim 7 wherein the metal alkoxide has the general formula $M(OR)_n$ wherein M is a metal capable of forming amphoteric oxides, R is a $C_1$-$C_3$ alkoxy group, and n is an integer.

9. The product of claim 8 wherein said acid is selected from acids whose esters resulting from the reaction with said metal alkoxide have a vapor pressure such that they will evaporate at a temperature below about 200°.

10. The product of claim 9 wherein said oxide particle growth terminator and solubilizer has a vapor pressure such that it will evaporate below 200° C.

11. The product of claim 7 wherein the metal oxide is a tantalum alkoxide, the acid is formic acid, the oxide particle terminator and solubilizer is a trialkyl chlorosilane and said cluster consists essentially of tantalum oxide clusters coated with trialkyl siloxane.

* * * * *